United States Patent
Araki et al.

(10) Patent No.: US 8,070,964 B2
(45) Date of Patent: Dec. 6, 2011

(54) MODIFIED SUBSTRATE AND PROCESS FOR PRODUCTION THEREOF

(75) Inventors: Miho Araki, Otsu (JP); Yoshiyuki Ueno, Otsu (JP); Hiroyuki Sugaya, Otsu (JP)

(73) Assignee: TORAY Industries, Inc., Tokyo (JP)

( * ) Notice: Subject to any disclaimer, the term of this patent is extended or adjusted under 35 U.S.C. 154(b) by 294 days.

(21) Appl. No.: 11/887,385

(22) PCT Filed: Mar. 28, 2006

(86) PCT No.: PCT/JP2006/306204
§ 371 (c)(1),
(2), (4) Date: Nov. 28, 2007

(87) PCT Pub. No.: WO2006/104117
PCT Pub. Date: Oct. 5, 2006

(65) Prior Publication Data
US 2009/0242477 A1 Oct. 1, 2009

(30) Foreign Application Priority Data
Mar. 29, 2005 (JP) ................................ 2005-094337

(51) Int. Cl.
*B01D 69/00* (2006.01)
*B01D 67/00* (2006.01)

(52) U.S. Cl. ......... 210/748.01; 210/500.23; 210/500.24; 210/500.35; 210/506; 210/636; 210/748.07; 210/748.08; 210/748.1; 422/22; 422/24

(58) Field of Classification Search ............. 210/500.23, 210/500.24, 500.35, 506, 636, 748.01, 748.07, 210/748.08, 748.1; 422/22, 24
See application file for complete search history.

(56) References Cited

FOREIGN PATENT DOCUMENTS

| EP | 0 672 424 A1 | 9/1995 |
|---|---|---|
| EP | 1 535 657 A1 | 6/2005 |
| JP | 63-209663 A | 8/1988 |
| JP | 7-328112 A | 12/1995 |
| JP | 2000-135421 A | 5/2000 |

OTHER PUBLICATIONS

Database WPI Week 199335, Derwent Publications Ltd., London, GB; AN 1993-277527, XP002479016.
Database WPI Week 199212, Derwent Publications Ltd., London, GB; AN 1992-091525, XP002479017.

*Primary Examiner* — John Kim
(74) *Attorney, Agent, or Firm* — Kubovcik & Kubovcik

(57) ABSTRACT

The present invention is characterized in that a base material comprises ester groups in the main chain and/or in the side chain(s), and comprises a polymer having hydrophobic groups. Particularly, the hydrophobic groups can be introduced by irradiating the base material with a radiation during the base material contacts an aqueous solution of a monohydric alcohol or an aqueous solution of an alcohol having not less than 2 hydroxyl groups, which is a monomer or a polymer, and which has one or more carbon atoms between the carbon atoms to each of which the hydroxyl group is bound in the monomer or in each monomer constituting the polymer.

3 Claims, 2 Drawing Sheets

MODIFIED SUBSTRATE AND PROCESS FOR PRODUCTION THEREOF

This application is a 371 of international application PCT/JP2006/306204 filed Mar. 28, 2006, which claims priority based on Japanese patent application No. 2005-094337 filed Mar. 29, 2005, which is incorporated herein by reference.

TECHNICAL FIELD

The present invention relates to a modified base material whose deterioration is small even when it is stored for a long time. The modified base material may suitably be applied to medical instruments, separation membranes for water treatment, instruments for biological experiments, bioreactors, molecular motors, protein chips, DNA chips and biosensors, or as parts of analyzers, antifouling films, antifouling resins and the like. Among these uses, it is preferably applied to medical instruments for which blood compatibility is required for a long time after radiation sterilization. That is, it may preferably be applied to modules for blood purification, such as artificial kidneys.

BACKGROUND ART

High blood compatibility is demanded for medical instruments which directly contact body fluid, such as artificial blood vessels, catheters, blood bags, contact lenses, intraocular lenses and artificial kidneys. In addition, it is also important that the blood compatibility of the medical instruments do not deteriorate or denature before the instruments are actually used.
Sterilization is required for most medical instruments. Because of the low residual toxicity and simplicity, radiation sterilization is widely used. On the other hand, since radiation sterilization is a high energy treatment, there is a problem in that it causes deterioration or denaturation of the materials constituting the medical instruments.
For example, it is known the effect of polyvinylpyrrolidone which is blended for giving blood compatibility to separation membranes is reduced by excessive crosslinkage or denaturation by the radiation (Non-patent Literature 1).
To reduce denaturation at the time of radiation sterilization, a method has been disclosed, in which a material is impregnated with a solution of an antioxidant such as sodium pyrosulfite (Patent Literature 2). A method in which a material is sterilized with γ-ray in the presence of glycerin (Patent Literature 3) and a method in which the material is sterilized with γ-ray in the presence of a dihydric alcohol such as polypropylene glycol (Patent Literature 4) have also been disclosed. Further, a method has been disclosed, in which a material having a low antithrombogenicity is subjected to radiation sterilization in the presence of a hydrophilic polymer and an antioxidant, thereby grafting the hydrophilic polymer to the material while inhibiting the excess denaturation of the hydrophilic polymer (Patent Literature 5).
These additives aim at inhibiting denaturation at the time of radiation, and the references are totally silent about the stabilization with time after the sterilization. Since a small amount of radicals remain after the radiation sterilization, there is a concern that materials constituting medical instruments denature during storage for a long time so that the blood compatibility is decreased. That is, even though the deterioration or denaturation of medical instruments at the time of radiation sterilization may be inhibited, the blood compatibility may have been deteriorated when the medical instruments are actually used.

On the other hand, as for the stability of medical instruments after radiation sterilization, a method has been disclosed, in which the amount of radicals contained in a membrane is made to be a prescribed level or less in blood purifiers (Patent Literature 6). In this method, excess hydrophilic polymers which may serve as sources of the radicals are removed. However, even if the excess hydrophilic polymers are removed, since some amounts of the hydrophilic polymers remain on the surface, the influence by the residual radicals cannot be avoided.
A method has also been disclosed, in which a chelating agent is added to a spinning solution in order to prevent a small amount of heavy metals from causing generation of radicals, which heavy metals are contaminated into the products during the membrane-forming step in the production of blood-purifying membranes (Patent Literatures 7 and 8). However, generation of radicals by the high energy of the radiation cannot be prevented, which radicals are directly generated in the membranes or generated by hydroxyl radicals generated from the ambient water molecules.
Thus, all of these methods are for inhibiting the generation of radicals by the radiation irradiation, and the material is not a radical-resistant material, so that they do not provide a fundamental solution. Thus, to develop a blood-compatible material having a high radical resistance was demanded, with which the above-mentioned deterioration of the blood compatibility does not occur, and which exhibits high blood compatibility even when the material is irradiated with a radiation at a dose several times the dose necessary for the sterilization.
Patent Literature 1: JP-A-H9-323031
Patent Literature 2: JP-B-2754203
Patent Literature 3: JP-B-2672051
Patent Literature 4: JP-B-3107983
Patent Literature 5: Japanese Republished International Publication No. WO04-018085
Patent Literature 6: JP-A-2000-296318
Patent Literature 7: JP-A-2005-334319
Patent Literature 8: JP-A-2005-342411

Problems which the Invention Tries to Solve

The present invention is to improve these drawbacks in the prior art and to provide a material whose blood compatibility is not deteriorated even if it is stored for a long time, and to provide a production process thereof.

Means for Solving the Problems

The present inventors intensively studied for attaining the above-described object, to complete the present invention. That is, the present invention is attained by the following constitutions (1)-(16):
(1) A process for producing a modified base material, characterized by irradiating a base material with a radiation during the base material contacts an aqueous solution of a monohydric alcohol(s) or an aqueous solution of an alcohol(s) having not less than 2 hydroxyl groups and having a molecular weight of less than 2000, the alcohol having not less than 2 hydroxyl groups being a monomer or a polymer, and being one having one or more carbon atoms between the carbon atoms to each of which the hydroxyl group is bound in the monomer or in each monomer constituting the polymer.
(2) The process for producing a modified base material, according to (1), characterized in that the alcohol has not more than 3 hydroxyl groups.

(3) The process for producing a modified base material, according to (1) or (2), characterized in that the base material comprises an ester group-containing polymer.
(4) The process for producing a modified base material, according to any one of (1) to (3), characterized in that the aqueous solution of alcohol(s) has a concentration of 0.0001% by weight to 40% by weight.
(5) The process for producing a modified base material, according to any one of (1) to (4), characterized in that the aqueous solution of alcohol(s) and/or the base material do(es) not substantially contain a water-soluble polymer.
(6) The process for producing a modified base material, according to any one of (1) to (5), characterized in that the ester group-containing polymer is a methacrylic polymer.
(7) The process for producing a modified base material, according to any one of (1) to (6), characterized in that the methacrylic polymer is poly(methyl methacrylate) or a derivative thereof.
(8) A modified base material after radiation sterilization, characterized in that the number of adhered human platelets is not more than 20 platelets/$(4.3\times10^3\ \mu m^2)$ and/or the relative adsorption ratio of fibrinogen is not more than 90%, after the modified material is irradiated with γ-ray at a dose of 25 kGy to 35 kGy under a condition that the base material is immersed in water.
(9) The modified base material according to (8), characterized in that the modified base comprises an ester group(s) and a polymer having a hydrophobic group(s).
(10) The modified base material according to (8) or (9), characterized in that the hydrophobic group is an alkane group.
(11) The modified base material according to any one of (8) to (10), characterized in that the polymer is a poly(methyl methacrylate) derivative.
(12) The modified base material according to any one of (8) to (11), characterized in that the modified base material is one for medical use.
(13) The modified base material according to any one of (8) to (12), characterized in that the modified base material is a part(s) constituting a module for blood purification.
(14) The modified base material according to any one of (8) to (13), characterized in that the modified base material is a hollow fiber membrane.
(15) The modified base material according to any one of (8) to (13), characterized in that the modified base material is a separation membrane.
(16) The modified base material according to any one of (13) to (15), characterized in that the module for blood purification is an artificial kidney.

EFFECT OF THE INVENTION

By the present invention, a material whose blood compatibility is not deteriorated even if it is stored for a long time can be provided.

Figure 1:
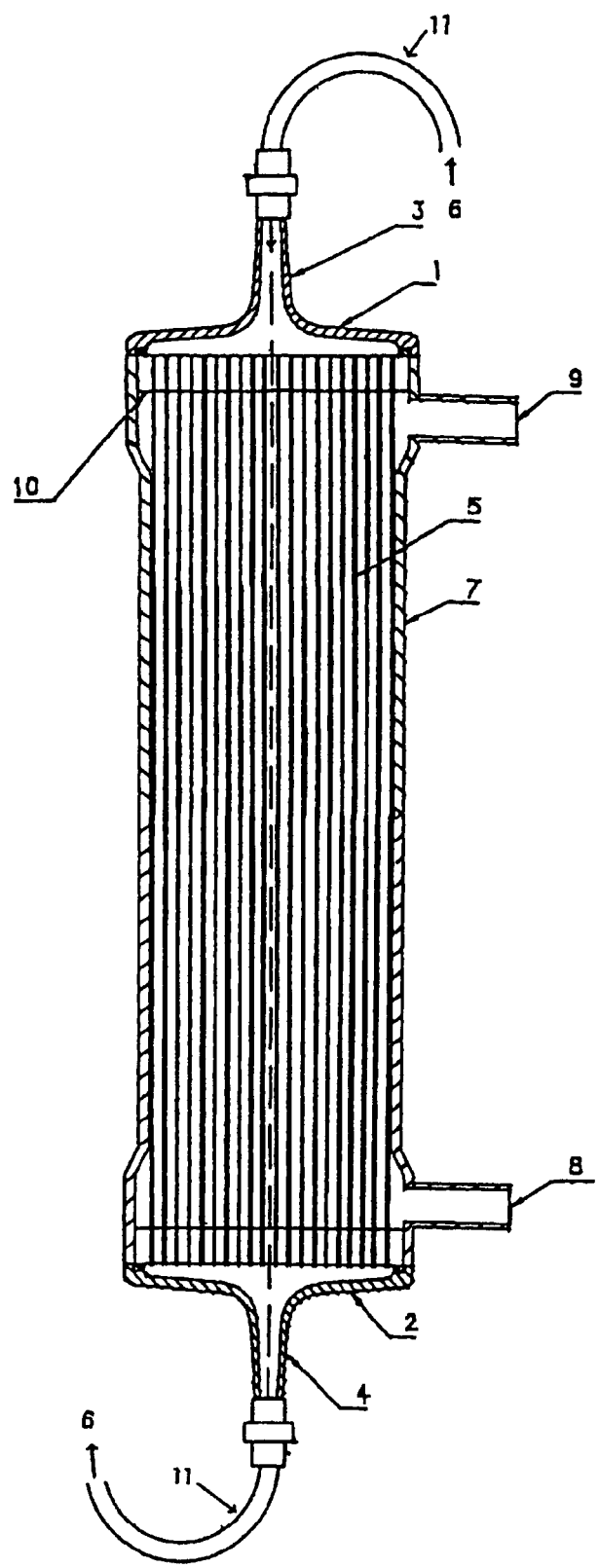
FIG. 1 shows an embodiment of an artificial kidney used in the present invention.

DESCRIPTION OF SYMBOLS 1. header at the side of artery
2. header at the side of vein
3. blood inlet
4. blood outlet
5. hollow fiber membranes
6. blood
7. module case
8. dialysate inlet
9. dialysate outlet
10. potted portion
11. blood circuit

BEST MODE FOR CARRYING OUT THE INVENTION

The present invention is characterized by irradiating a base material used for medical instruments, especially a base material comprising an ester group-containing polymer, with a radiation during the base material contacts an aqueous solution of a specific alcohol. As the radiation, α-ray, β-ray, γ-ray, X-ray, ultraviolet light, electron beam or the like may be employed. It is necessary to sterilize medical instruments such as artificial kidneys. In recent years, radiation sterilization is widely used because of the low residual toxicity and simplicity, and γ-ray and electron beam are suitably employed. Thus, since sterilization is simultaneously carried out by applying the method of the present invention, it is preferred to apply the present invention to the base materials for medical instruments.

As for the dose employed for sterilization of medical instruments, it is said that a dose of 15 kGy to 35 kGy is appropriate. Since the modified base material according to the present invention is excellent in radical resistance, even if the modified base material after radiation sterilization is immersed in water and irradiated again with γ-ray at a dose of 25 kGy to 35 kGy, the modified base material maintains good blood compatibility. The term "good blood compatibility" herein means that the modified base material attains the number of adhered human platelets of not more than 20 platelets/$(4.3\times10^3\ \mu m^2)$, preferably not more than 15 platelets/$(4.3\times 10^3\ \mu m^2)$, still more preferably not more than 10 platelets/$(4.3\times10^3\ \mu m^2)$, and/or a relative adsorption ratio of fibrinogen is not more than 90%, preferably not more than 70%, still more preferably not more than 50%.

The number of adhered human platelets herein means the value measured by the following method:

A sample to be measured is attached to the inside of an cylindrical tube of which bottom has a diameter of about 18 mm. Heparin sodium is added to the cylindrical tube to a concentration of 50 U/ml, and 1.0 ml of venous blood of a normal individual is then added, followed by shaking the resulting mixture at 37° C. for 1 hour (this operation is preferably started within 10 minutes from collection of the blood). Blood components are then fixed with physiological saline containing glutaraldehyde, and the resulting sample is then dried under reduced pressure for 10 hours after washing the sample with distilled water. A platinum-palladium thin film is formed in hollow fiber membranes by sputtering to obtain a sample, and the inner surfaces of the membranes are observed with a field emission scanning electron microscope (the magnification is preferably ×1500), followed by counting the number of adhered platelets in one visual field ($4.3\times 10^3\ \mu m^2$). The mean of the numbers of adhered platelets counted in different 10 visual fields is defined as the number of adhered platelets (platelets/$(4.3\times10^3\ \mu m^2)$).

The relative adsorption ratio of fibrinogen is measured by the following method:

After contacting a sample with a solution of fibrinogen in PBS, the adsorbed fibrinogen is marked with an HRP-labeled anti-human fibrinogen antibody, and the resultant is colored with TMB one solution. Since the coloring reaction proceeds with time, the reaction is stopped with 1N hydrochloric acid while observing the coloring. Absorbance at 450 nm is then measured.

To 97 parts by weight of chloroform, 1 part by weight of iso-poly(methyl methacrylate) and 2 parts by weight of syn-poly(methyl methacrylate) were added and dissolved at room temperature to obtain a solution for forming a film. To a glass Petri dish (diameter: 90 mm), the obtained solution for forming a film is poured. The solution is left to stand overnight at room temperature thereby evaporating chloroform, to form a film. The film is then peeled off from the Petri dish to obtain a poly(methyl methacrylate) film. The relative adsorption ratio of fibrinogen is defined as the relative ratio (%) of the absorbance of the sample taking as 100 the absorbance of the film obtained by immersing the thus obtained poly(methyl methacrylate) film in deaerated water and irradiating the film with γ-ray at a dose of 25 kGy.

The details of the measuring methods of the number of adhered human platelets and the relative adsorption ratio of fibrinogen will be described later in Examples.

The reason why the method for evaluation of the radical resistance, in which the modified base material is irradiated with γ-ray while immersing the modified base material in water, is excellent is that the conditions are severer than in cases where the modified base material is irradiated in the air. That is, this is because that for the denaturation of the material, the indirect effect through hydroxy radicals generated from the ambient water molecules is larger than the direct effect through the radicals generated in the material itself by the high energy of the γ-ray.

The term "modified base material" as used in the present invention means a molded polymer material synthesized to attain an excellent blood compatibility or a molded polymer material or the like whose surface was subjected to a reaction or whose surface has a coating to attain a good blood compatibility. Examples of the form thereof include, but not limited to, fibers, films, resins, separation membranes and the like.

The modified base material according to the present invention preferably has ester groups in its main chain and/or in a side chain(s), and preferably comprises a polymer having a hydrophobic group(s) as a constituent.

To promote the blood compatibility of the modified base material according to the present invention, existence of a polymer containing an ester group(s) is thought to be preferred. That is, ester group is a hydrophilic functional group and hydration layer is formed around it. It is generally thought that the reason why platelets or the like hardly adhere to a hydrophilic material is that a hydration layer is formed on the surface of the material. It is known that the waters hydrated to such a base material includes two types of waters, that is, a water called nonfreezable water which strongly interacts with the material and which does not freeze even if cooled to about −80° C., and freezable bound water of which interaction is relatively weak and which is subjected to exchange reaction with bulk free water. It is known that among the hydrophilic materials, the surface of the materials having a large amount of freezable bound water is a dynamic surface on which the exchange reaction between the bound water and the bulk free water continuously occurs, so that platelets or the like hardly adhere thereto. It is said that the interaction between ester group and water molecules is weaker than the interaction between amide group or hydroxyl group and water. That is, it is thought that the surface of the material may be covered with freezable bound water due to the ester groups.

Although the detailed reason why the modified base material according to the present invention has a high radical resistance is not clear, the existence of hydrophobic groups is thought to be important. That is, even if the polymer is subjected to denaturation such as decomposition by the irradiation of γ-ray, the state in which the ester groups are exposed to the water at the surface may be retained by virtue of the interaction between the hydrophobic groups.

A method is also known, in which a diffuse layer of a water-soluble polymer is formed on the surface of the material, thereby exhibiting blood compatibility. In this case too, it is said that platelets or the like hardly adhere because the surface is a dynamic surface due to the molecular movements of the water-soluble polymer at the surface of the material.

However, in the present invention, in cases where a large amount of such a water-soluble polymer is blended in the modified base film, radical resistance is not obtained. The reason therefor is thought to be as follows: In cases where the water-soluble polymer is crosslinked by the radiation, the molecular movements decrease, which leads to the deterioration of the blood compatibility. Further, if the water-soluble polymer is degraded by the radiation, defects are formed in the diffuse layer, which leads to the deterioration of the blood compatibility. Further, because the molecule is large, even if a reaction such as crosslinking occurs even only at one site anywhere, the influence thereof given to the whole is large. That is, the diffuse layer of water-soluble polymer can be said to be sensitive to radiation. Thus, radical resistance cannot be obtained in cases where a large amount of water-soluble polymer is blended in the modified material presumably because the water-soluble polymer covers the ester groups.

Thus, in the present invention, it is preferred that a water-soluble polymer be substantially not contained in the modified base material. The term "substantially" herein means the degree that the water-soluble polymer does not influence on the radical resistance, and a small amount of water-soluble polymer is allowed to be contained. Although the content of the water-soluble polymer in the modified base material varies depending on the type of the water-soluble polymer and the polymer containing an ester group(s) so that the content cannot be generalized, the content is not more than 5% by weight, preferably not more than 1% by weight, still more preferably not more than 0.1% by weight.

The term "water-soluble polymer" herein means a substance having a solubility in water at 25° C. of preferably not less than 0.01% by weight, more preferably not less than 0.1% by weight, which substance has a molecular weight of not less than 2000. Examples of the water-soluble polymers include polyvinylpyrrolidone, polyethylene glycols, polyvinyl alcohol and the like.

In the modified base material according to the present invention, as for the examples of the polymers containing ester groups, examples of the polymers containing ester groups in their main chain include polyesters; terephthalic acid-based polymers such as polyethylene terephthalate, polytrimethylterephthalate and polybutylene terephthalate; polylactic acid; polybutylene succinate; poly caprolactone and the like. Examples of the polymers having ester groups in the side chains include naturally occurring polymers such as polyamino acids, cellulose diacetate and cellulose triacetate; vinyl polymers such as polyvinyl acetate and poly(methyl acrylate); and methacrylic and acrylic polymers such as poly(methyl methacrylate), poly(ethyl methacrylate), poly(propyl methacrylate), 2-hydroxyethyl methacrylate, and 2-ethylhexyl acrylate. The ester group-containing polymer may be a derivative such as a copolymer or graft with other monomers, as long as it contains the units such as those mentioned above. The base material comprising such an ester group-containing polymer may comprise the polymer mentioned above individually or may comprise a mixture of the polymers.

The modified base material of the present invention is characterized in that it comprises a polymer to which a hydrophobic group(s) is(are) bound, in addition to the ester group-containing polymer. As the hydrophobic group, saturated hydrocarbon (alkane) groups are preferred, and saturated hydrocarbon groups having not less than two carbon atoms are especially preferred. On the other hand, since the hydrophobic moiety may be exposed to the surface if the carbon number is large, the carbon number is not more than 12, preferably not more than 8, still more preferably not more than 4. The hydrocarbon group may be linear or branched. However, hydrocarbon groups having an unsaturated bond(s) may activate the blood. Further, since unsaturated bond may generate radicals, and the radical resistance is not high, the hydrocarbon groups having an unsaturated bond(s) are not preferred.

An example of the method for introducing the hydrophobic group(s) is the method in which a hydrophobic monomer(s) and an ester group-containing monomer(s) are copolymerized. For example, by radical polymerizing methyl methacrylate and ethylene, a copolymer of poly(methyl methacrylate) and polyethylene can be obtained. Although the composition ratio of the copolymer cannot be generalized because it varies depending on the types of the monomers, the percentage of the hydrophobic group(s) with respect to the ester group(s) is not more than 50 mol %, preferably not more than 10 mol %, still more preferably not more than 1 mol %. For example, in case of a copolymer between methyl methacrylate and ethylene, the percentage of the ethylene with respect to the methyl methacrylate is preferably not more than 20 mol %.

Another example of the method for introducing the hydrophobic group(s) is the method in which a hydrophobic group(s) is(are) introduced to the ester group-containing polymer. In this case, the sites to which the hydrophobic group(s) is(are) bound is(are) not restricted, and it(they) may be bound to the main chain of the polymer or may be bound to a side chain(s). Further, a linker moiety such as ether group or the like may exist between the hydrophobic group and the polymer. For example, ethoxy groups may be introduced to poly(methyl acrylate) by mixing poly(methyl acrylate) and diethyl peroxide, and allowing them to react at a high temperature under high pressure. In general, graft polymerization is more preferably employed than copolymerization because the physicochemical properties of the main chain are likely to remain. Although the hydrophobic group(s) in the polymer increase radical resistance, if the percentage thereof is too large, the hydrophilicity of the surface is decreased, and the blood compatibility is also decreased accordingly. Therefore, although the percentage of the hydrophobic group(s) cannot be generalized because it varies depending on the types of the polymer main chain and the hydrophobic group(s), in cases where the polymer contains an ester group(s), the percentage of the hydrophobic group(s) with respect to the ester group(s) is not more than 80 mol %, preferably not more than 20 mol %, still more preferably not more than 5 mol %.

Another method for introducing the hydrophobic group(s) into the polymer is a method using radiation graft polymerization. For example, an alcohol(s) is(are) preferably employed as the compound(s) giving the above-described saturated hydrocarbon group(s), and the alcohol(s) may be grafted to the polymer by immersing the ester group-containing base material in an aqueous solution of the alcohol(s) and irradiating the base material with a radiation. This method is especially preferred because it is simple. Thus, by modifying the base material with radiation, a modified base material having a high radical resistance can be obtained, the radicals being generated by γ-ray.

Among the alcohols having not less than two hydroxyl groups, those such as ethylene glycol and glycerin, in which the carbon atoms to which the hydroxyl groups are bound, respectively, are adjacent to each other, unsaturated bond(s) is(are) likely to be generated by the radiation. This is presumably because that radicals are likely to be generated on the carbon atom to which the hydroxyl group is bound, and unsaturated bond is likely to be generated if the carbon atoms to which hydroxyl groups are bound, respectively, are adjacent.

When a hydrocarbon group(s) having an unsaturated bond(s) is(are) grafted to the polymer, not only the blood compatibility is deteriorated, but also radical resistance is poor because radicals are likely to be generated due to cleavage of the unsaturated bond(s), as described above.

Therefore, as the alcohol, monohydric alcohols and alcohols having not less than 2 hydroxyl groups and having one or more carbon atoms between the carbon atoms to each of which the hydroxyl group is bound are preferably employed, and monohydric alcohols are preferred. Further, if the alcohol has not less than 4 hydroxyl groups, since the number of sites at which radicals are generated is increased, the probability that unsaturated bonds are formed is thought to be increased. Therefore, alcohols having not more than 3 hydroxyl groups are preferably employed.

Specific examples of monohydric alcohols include primary alcohols such as methanol, ethanol, 1-propanol, 1-butanol, 1-pentanol, 1-hexanol and the like; and dihydric and trihydric alcohols such as isopropanol and t-butanol. Examples of the alcohols having not less than 2 hydroxyl groups include 1,3-propanediol, 1,4-butanediol, pentaerythritol and the like. The class of alcohol (whether the alcohol is primary, secondary or tertiary alcohol) is not limited.

If the alcohol concentration of the aqueous alcohol solution is too low, the grafting reaction may not easily occur. On the other hand, if the alcohol concentration is too high, reaction between alcohol molecules occur so that the grafting reaction to the polymer may not easily occur. Therefore, the concentration of the aqueous alcohol solution is preferably not less than 0.0001% by weight, more preferably not less than 0.001% by weight. On the other hand, the concentration is preferably not more than 40% by weight, more preferably not more than 10% by weight, still more preferably not more than 0.1% by weight.

As for the molecular weight of the alcohol, if the molecular weight is large, the grafted alcohol may cover the ester groups in the surface of the material. Therefore, it is not preferred to use a high molecular alcohol such as polyvinyl alcohol, polyallyl alcohol or the like. Thus, the molecular weight of the alcohol is preferably less than 2000, more preferably not more than 200. In cases where the molecular weight of the alcohol has a distribution, the molecular weight means the weight average molecular weight. The molecular weight can be determined by using a mass spectrometer or gel permeation chromatography.

In cases where the above-described water-soluble polymer is contained in the aqueous alcohol solution, the water-soluble polymer may be grafted to the surface of the material to cover the ester groups. Therefore, if the water-soluble polymer is contained in the aqueous alcohol solution, the effect to modify the base material in the present invention cannot be obtained. However, the water-soluble polymer may be contained in an amount which does not adversely affect the effect of the present invention. Although the concentration of the water-soluble polymer differs depending on the type of the water-soluble polymer and the ester group-containing polymer, and so cannot be generalized, it is not more than 100 ppm by weight, preferably not more than 10 ppm by weight, still more preferably not more than 1 ppm by weight.

As the radiation used for the grafting reaction, α-ray, β-ray, γ-ray, X-ray, ultraviolet light, electron beam or the like is employed, as mentioned above. As for the dose of the radiation, an energy for initiating the grafting reaction is necessary. The dose of the radiation with which the grafting reaction occurs differs depending on the alcohol and the structure of the polymer to be grafted. Thus, although the necessary dose cannot be generalized, a dose of not less than 5 kGy, more preferably not less than 15 kGy is preferred in most cases. On the other hand, if the dose of radiation is too high, side reactions other than the grafting reaction may occur. Therefore, the dose of radiation is preferably not more than 50 kGy, more preferably not more than 35 kGy.

The ester group-containing polymer to which the method for grafting the alcohol(s) by the radiation may be applied is not restricted, and the method may be applied to polyesters; terephthalic acid-based polymers such as polyethylene terephthalate, polytrimethyl terephthalate and polybutylene terephthalate; polylactic acid; polybutylene succinate; poly caprolactone; vinyl polymers such as polyvinyl acetate and poly(methyl acrylate); naturally occurring macromolecules such as poly amino acids, cellulose diacetate and cellulose triacetate; and methacrylic and acrylic polymers such as poly(methyl methacrylate), poly(ethyl methacrylate), poly(propyl methacrylate), 2-hydroxyethyl methacrylate and 2-ethylhexyl acrylate. Among these, polymers which are degraded by radiation are especially preferably employed because the efficiency of grafting of the alcohol(s) is high. Examples of such polymers include polylactic acid, poly(butylene succinate), polycaprolactone, poly(methyl methacrylate), poly(ethyl methacrylate) and poly(propyl methacrylate). In view of the availability and the like, poly(methyl methacrylate) is especially preferably employed.

Since the possibility that blood compatibility of the modified base material of the present invention is deteriorated is low even if it is stored for a long time, it may be suitably used in medical instruments. Since adsorption of organic substances and the like to a material having a high blood compatibility is small, the modified base material may also be suitably used in separation membranes for water treatment, instruments for biological experiments, bioreactors, molecular motors, DDSs (drug delivery systems), protein chips, DNA chips and biosensors, or as parts of analyzers, antifouling films, antifouling resins and the like. Since the technology of the present invention may be applied to methacrylic polymers, it may be suitably applied to antifouling films and antifouling resins which require transparency and antifouling property.

Among the medical instruments, those in which the modified base material may be suitably used include separation membranes for medical use, artificial blood vessels, catheters, blood bags, contact lenses, intraocular lenses, surgical aid tools, modules for blood purification and the like.

Modules for blood purification are modules having a function to remove wastes and toxic substances in the blood by adsorption, filtration and/or diffusion when the blood is circulated ex vivo, and examples thereof include artificial kidneys and exotoxin-adsorbing columns.

The form of the separation membrane contained in the modules for blood purification is not restricted, and may be in the form of flat membrane, hollow fiber membrane or the like.

In view of the treatment efficiency, that is, to obtain a large surface area contacting the blood, the membrane is preferably in the form of hollow fiber membrane. Thus, the modified base material of the present invention may be suitably used as a base material for medical use. The base material for medical use is one which contacts components originated from living body, such as body fluid or blood, and preferably has a high blood compatibility and safety. The term "base material for medical use" herein means a member constituting a medical instrument.

There are various processes for producing the modules for blood purification according to the present invention depending on the use thereof, and the process may be roughly grouped into a step of producing a separation membrane for blood purification, and a step for incorporating the separation membrane into a module.

In cases where the modified base material according to the present invention is a separation membrane, after synthesizing a polymer having an ester group(s) in its main chain and/or in a side chain(s) and having a hydrophobic group(s), the polymer may be molded into a separation membrane. Alternatively, after molding a separation membrane, the hydrophobic groups may be grafted to the separation membrane utilizing the grafting reaction by irradiating the membrane with a radiation. Using the grafting reaction is preferred because sterilization can be carried out simultaneously with the grafting reaction. That is, in cases where an alcohol is used as the compound giving hydrophobic groups, the module may be filled with the alcohol after incorporating the separation membrane into the module, and the membrane may be irradiated with a radiation. Carrying out the radiation irradiation after modularization is preferred because sterilization can be carried out simultaneously. However, if the alcohol concentration is high, unreacted alcohol may remain in the final product. Therefore, the alcohol concentration is not more than 1% by weight, preferably not more than 0.5% by weight, still more preferably not more than 0.1% by weight. On the other hand, the alcohol concentration is preferably not less than 0.0001% by weight, preferably not less than 0.001% by weight as described above (the upper limit is different from that described above because the cases where sterilization of medical instruments is simultaneously carried out are described here).

One example of the process for producing the hollow fiber membrane module used for artificial kidneys will now be described. Processes for producing hollow fiber membranes contained in artificial kidneys include the following processes: That is, 5 parts by weight of iso-poly(methyl methacrylate) and 20 parts by weight of syn-poly(methyl methacrylate) are added to 75 parts by weight of dimethylsulfoxide, and are dissolved therein under heat to obtain a membrane-forming liquid. The thus obtained membrane-forming liquid is extruded from an orifice type coaxial cylindrical mouthpiece, and the extruded material is introduced into a coagulation bath containing 100% water after passing 300 mm in the air, thereby a hollow fiber membrane may be obtained. In this case, as the gas introduced into the inside of the fiber, dry nitrogen is used.

The method for incorporating the hollow fiber membrane into the module is not restricted, and one example thereof is as follows: First, the hollow fiber membrane is cut into pieces having a required length, and a requisite number of the obtained fibers are bundled, followed by placing the resulting bundle into a cylindrical case. Then the both ends of the case are capped with temporary caps, and a potting material is introduced into the both end portions of the hollow fiber membranes. In this case, a method in which the potting material is introduced while rotating the module with a centrifuge is a preferred method because the potting material is uniformly packed. After the potting material is solidified, the both end portions are cut such that the both ends of the respective hollow fibers are opened, thereby obtaining a hollow fiber membrane module.

As the radiation, α-ray, β-ray, γ-ray, X-ray, ultraviolet light, electron beam or the like is employed. Medical instruments such as artificial kidneys are required to be sterilized. In recent years, radiation sterilization is widely used because of the low residual toxicity and simplicity, and γ-ray and electron beam are suitably employed. Thus, since sterilization is simultaneously carried out by applying the method of the present invention, it is preferred to apply the present invention to the base materials used in medical instruments. For example, to sterilize a module for blood purification with γ-ray, a radiation dose of not less than 15 kGy is preferred. It should be noted, however, in cases where the material is used in a use not requiring sterilization, the dose is not restricted thereto.

One embodiment of the basic structure of an artificial kidney using the thus obtained hollow fiber membrane module is shown in FIG. 1. In a cylindrical module case 7, a bundle of hollow fiber membranes 5 is inserted, and the both end portions of the hollow fibers are sealed with potted portions 10. The case 7 is provided with an inlet 8 and outlet 9 of dialysate, and the dialysate, physiological saline, filtered water or the like passes through the outside of the hollow fiber membranes 5. The ends of the case 7 are provided with a header 1 at the side of artery and a header 2 at the side of vein, respectively. Blood 6 is introduced through a blood inlet 3 formed in the header 1 at the side of artery and guided into the inside of the hollow fiber membranes 5 by the header 1 at the side of artery having a funnel shape. The blood 6 after being filtered through the hollow fiber membranes 5 is gathered by the header 2 at the side of vein, and discharged through a blood outlet 4. To the blood inlet 3 and the blood outlet 4, a blood circuit 11 is connected.

EXAMPLES

The present invention will now be described in more detail by way of examples. However, the present invention is not restricted to the examples.
1. Preparation of Base Material
(1) Hollow Fiber Membrane Module Five parts by weight of iso-poly(methyl methacrylate) and 20 parts by weight of syn-poly(methyl methacrylate) were added to 75 parts by weight of dimethylsulfoxide, and were dissolved therein under heat to obtain a membrane-forming liquid. The thus obtained membrane-forming liquid was extruded from an orifice type coaxial cylindrical mouthpiece, and the extruded material was introduced into a coagulation bath containing 100% water after passing 300 mm in the air having a dry zone atmosphere, to obtain a hollow fiber membrane. In this case, as the gas introduced into the inside of the fiber, dry nitrogen was used. The inner diameter of the obtained hollow fiber membrane was 0.2 mm, and the thickness thereof was 0.03 mm.

The obtained 12,000 hollow fibers were inserted in a cylindrical plastic case having dialysate inlet and dialysate outlet as shown in FIG. 1, and both ends thereof were sealed with urethane resin, to prepare a hollow fiber membrane module for artificial kidneys, which had an membrane area of 1.6 m².

The membrane area is the value calculated by multiplying inner surface area of the hollow fiber calculated from the inner diameter thereof by the number of fibers and by the length of the end face.
(2) Films Films were prepared from poly(methyl methacrylate) and polylactic acid, respectively, by the methods described below. It should be noted that films formed from a polymer other than these polymers may be prepared by appropriately selecting a solvent for dissolving the polymer, and reduction of pressure or heating may be performed so that the solvent is evaporated.
(a) Poly(methyl methacrylate) Film To 97 parts by weight of chloroform, 1 part by weight of iso-poly(methyl methacrylate) and 2 parts by weight of syn-poly(methyl methacrylate) were added and dissolved in the chloroform at room temperature to obtain a film-forming solution. To a glass Petri dish (diameter 90 mm), 10 g of this film-forming solution was poured. The solution was left to stand overnight at room temperature to evaporate chloroform, thereby forming a film. The film was then peeled off from the Petri dish to obtain a poly(methyl methacrylate) film for platelet adhesion test.
(b) Polylactic Acid Film To 97 parts by weight of chloroform, 1.5 parts by weight of D-polylactic acid (produced by Cargill Dow, weight average molecular weight 150,000) and 1.5 parts by weight of L-polylactic acid (produced by Funakoshi, weight average molecular weight: 100,000) were added and dissolved in the chloroform at room temperature to obtain a film-forming solution. Thereafter, the same operations as in (a) described above were repeated to obtain a polylactic acid film for platelet adhesion test.
2. Method for Preparing Modified Base Material
(1) Process for Producing Modified Hollow Fibers The alcohol or polymer used for the modification was dissolved in deaerated pure water to obtain an aqueous solution. The term "deaerated water" herein means the water subjected to stirring for 30 minutes to 1 hour under pressure reduced by 500 to 760 mmHg at room temperature. The oxygen dissolved in water serves as a radical initiator when irradiated with γ-ray. Therefore, using water which has not been deaerated is one of the causes of fluctuation of the results of the experiments thereafter, so that attention should be paid.

The thus obtained aqueous solution was introduced into the hollow fiber membrane module prepared in 1.(1) through the blood inlet 3, then guided to the dialysate outlet 9 through the blood outlet 4, and was discharged from the dialysate inlet 8, thereby filling the hollow fiber membrane module with the aqueous solution. The flow rate of the aqueous solution at this time was 450 mL/min, and the time for flowing the solution was 1 minute. The resulting hollow fiber membrane module was irradiated with γ-ray at a dose of 25 kGy to simultaneously carry out modification of the hollow fiber membrane and sterilization of the hollow fiber membrane module.

Figure 2:
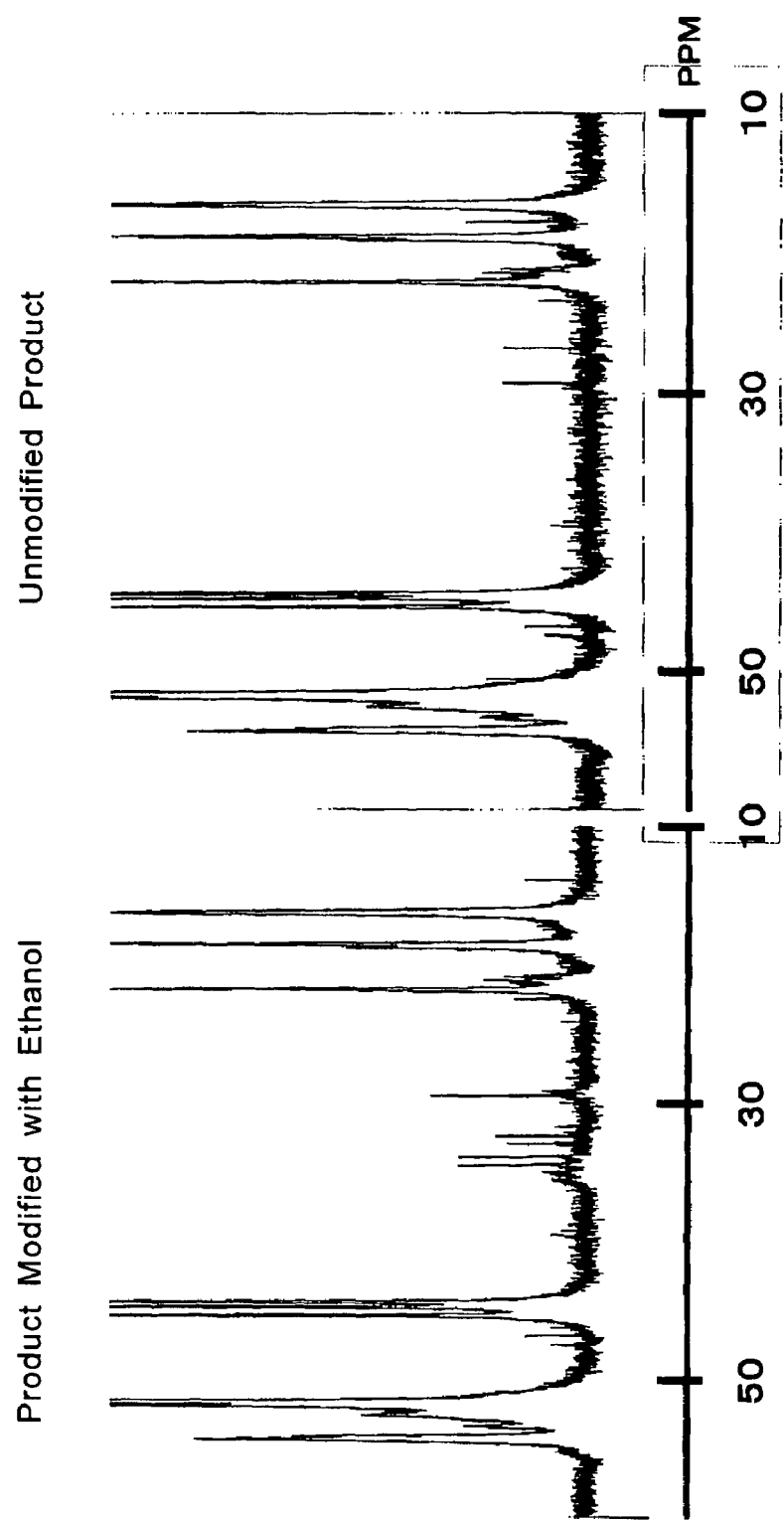
FIG. 2 shows a $^{13}C$—NMR spectrum.

The hollow fiber membrane module was filled with aqueous 0.1% by weight solution of $CH_3$—$^{13}CH_2$—OH labeled with $^{13}C$ by the method described above, and the resulting module was irradiated with γ-ray at a dose of 25 kGy. The hollow fiber membranes were cut out and 2.0 g aliquot thereof was weighed after being dried in a vacuum dryer (produced by Tokyo Rikakikai). The thus obtained hollow fiber membranes were immersed in 50 mL of mixed solvent of methanol:chloroform=4:1 (by volume), and the resulting mixture was stirred for 15 minutes. The residue which was not dissolved was removed, and the solvent was evaporated to obtain a dried product. The obtained dried product was dissolved in deuterated chloroform (containing 1% tetramethylsilane, produced by Sigma Aldrich Japan), and $^{13}$C-NMR analysis was carried out. As shown in FIG. 2, peaks of alkane groups were observed in the range of 30 to 40 ppm, so that it was confirmed that modification was attained. On the other hand, the same operations as described above were repeated on the hollow fiber membranes obtained from hollow fiber membrane module filled with pure water and irradiated with D-ray at a dose of 25 kGy. As a result, as shown in FIG. 2, no peaks were observed in the range of 30 to 40 ppm.

(2) Method for Preparing Modified Films

The alcohol to be used for modification was dissolved in deaerated pure water to prepare an aqueous solution. The films prepared in 1.(2) were immersed in the aqueous alcohol solution and irradiated with γ-ray at a dose of 25 kGy. The films and a test tube were washed with pure water, and dried in the air.

3. Measuring Methods and Testing Methods

Two samples of the modified base material were provided for each level. One of the samples was not irradiated with γ-ray in water, and the other sample was irradiated with γ-ray in water. By subjecting both of these films to the platelet adhesion test and the fibrinogen adhesion test, the blood compatibility and the radical resistance of the modified base material were evaluated.

(1) Irradiation of γ-Ray in Water

After well washing the modified base material after radiation sterilization with water, the modified base material was immersed in deaerated water.

In cases where the modified base material was the hollow fiber membranes in the module, water was introduced into the module from the blood inlet 3, then guided to the dialysate outlet 9 through the blood outlet 4, and was discharged from the dialysate inlet 8, thereby washing the hollow fiber membranes. The flow rate was 450 mL/min, and the washing time was 10 minutes. Thereafter, deaerated pure water was flown in the same manner, thereby filling the hollow fiber membrane module with deaerated pure water. The flow rate was 450 mL/min and the flow time was 5 minutes.

In cases where the modified base material was a film, the film was washed 3 times or more with water in an amount of about 100 times the weight of the film per wash. Thereafter, the film was immersed in deaerated pure water.

The modified base material immersed in water as described above was irradiated with γ-ray at a dose of 25 kGy to 35 kGy.

In cases where a modified base material after radiation sterilization is subjected to irradiation with γ-ray in water, it is preferred to carry out the irradiation within one year from the sterilization. Further, the sample to be subjected to the platelet adhesion test or fibrinogen adhesion test is preferably one which was subjected to the sterilization within one year before the test.

(2) Method of Platelet Adhesion Test

A double-stick tape was adhered to a polystyrene disk (in the form of film) having a diameter of 18 mm, and hollow fiber membranes were adhered thereto. The adhered hollow fiber membranes were cut into semicylindrical shape with a single edged knife to expose the inner surfaces of the hollow fiber membranes. In cases where the sample was a film, the film was cut into a square with a size of 3 to 5 mm, and the cut film was adhered to the disk (If there is a stain, scratch, fold or the like on the surface of the hollow fiber membranes or the film, platelets are adhered thereto, so that correct evaluation may not be attained. Thus, attention should be paid).

The resulting disk was attached to a Falcon (registered trademark) tube cut into cylindrical shape (diameter 18 mm, NO. 2051), such that the surface on which the hollow fiber membranes or the film were adhered was located in the inside of the cylinder, and the gap at the portion at which the disk was attached was closed with Parafilm. After washing the inside of the cylinder with physiological saline, the inside of the cylinder was filled with physiological saline. Venous blood was collected from a normal individual, and heparin sodium injection (produced by Ajinomoto) was immediately added thereto to a concentration of 50 U/ml. After discarding the physiological saline in the cylinder, 1.0 ml of the blood was placed in the cylinder within 10 minutes from the blood collection, and the blood was shaken at 37° C. for 1 hour. Thereafter, the hollow fiber membranes were washed with 10 ml of physiological saline, and the blood components were fixed with physiological saline containing 2.5% by volume of glutaraldehyde (produced by Nacalai Tesque), followed by washing the membranes with 20 ml of distilled water. The washed hollow fiber membranes were dried under reduced pressure for 10 hours at normal temperature at an absolute pressure of 66 Pa. The thus obtained disk was adhered to the stage of a scanning electron microscope with a double-stick tape. Thereafter, a thin film of platinum-palladium was formed on the surfaces of the hollow fiber membranes or of the film by sputtering to obtain a sample. The inner surfaces of the hollow fiber membranes or the surface of the film were observed with a field emission scanning electron microscope (S800 produced by Hitachi) at a magnification of ×1500, and the number of adhered platelets in one visual field ($4.3 \times 10^3$ μm$^2$) was counted. The number of adhered platelets in 10 visual fields in the center portion in the longitudinal direction of the hollow fibers or in the central portion of the film was counted, and the average thereof was defined as the number of adhered platelets (platelets/($4.3 \times 10^3$ μm$^2$)). The central portion was observed because a blood pool is likely to be formed in the end portions in the longitudinal direction of the hollow fibers and in the peripheral portions of the film.

In the platelet adhesion test, a positive control and negative control are tested in each experiment in order to check whether or not the test is properly carried out. The positive control is a sample known as a material to which a large number of platelets are adhered. The negative control is a sample known as a material to which only a small number of platelets are adhered. As the positive control, the hollow fiber membranes in "Filtryzer" BG-1.6U, an artificial kidney produced by TORAY, are employed. As the negative control, the hollow fiber membranes in artificial kidney PS-1.6UW produced by Kawasumi Laboratories are employed. Under the above-described experimental conditions, only when the number of platelets adhered to the positive control is not less than 40 (platelets/($4.3 \times 10^3$ μm$^2$)), and the number of platelets adhered to the negative control is not more than 5 (platelets/($4.3 \times 10^3$ μm$^2$)), the measured value is adopted. If the number of the platelets adhered to the control is outside the above-described range, the test is carried out again because it is thought that the blood was not fresh or excessive activation of the blood occurred.

If the number of adhered platelets is not more than 20 (platelets/$4.3 \times 10^3$ μm$^2$)) in this experiment, the blood compatibility is thought to be good.

(3) Method for Testing Fibrinogen Adsorption (a) Preparation of Sample

Due to adsorption of fibrinogen to the vessel, experimental results fluctuate. Therefore, after dissolving the modified base material to be subjected to the test, the resulting solution was directly coated on the inner wall of an Eiken tube (No. 2, produced by Eiken Kizai).

That is, the modified base material was dissolved in an appropriate solvent. The concentration is preferably about 3% by weight. An epoxy resin was coated on the inside of the Eiken tube, and warmed in an oven at 80° C. for 2 hours to heat-cure the resin, followed by allowing the resin to cool. The portion coated with the epoxy resin was again coated with the solution of the modified base material, and the resultant was warmed in an oven at 50° C. for 2 hours to solidify the solution, thereby to obtain a sample for the fibrinogen adsorption test.

(b) Measurement of Relative Adsorption of Fibrinogen

A solution of fibrinogen (fibrinogen originated from human, produced by Sigma Chemical) in PBS(−) (Dulbecco's PBS(−) powder, produced by Nissui Pharmaceutical) having a fibrinogen concentration of 1000 ng/mL was prepared. An HRP-labeled anti-human fibrinogen antibody was 10.000-fold diluted with aqueous Tween solution in PBS(−) (a solution prepared by dissolving 50 μL of polyoxyethylene (20) sorbitan monolaurate (produced by Wako Pure Chemicals, corresponding to Tween 20, a trademark of ICI) in IL of PBS(−)).

To each dried test tube coated with the respective modified base material, 100 μL each of fibrinogen solution in PBS(−) was added, and the resultant was left to stand at room temperature for 60 minutes. Each test tube was then washed 5 times with PBS(−) Tween. Then 100 μL each of the HRP-labeled anti-fibrinogen antibody was added, and the resultant was left to stand at room temperature for another 60 minutes. Each test tube was then again washed 5 times with PBS(−) Tween, and 100 μL each of TMB one solution (produced by Promega) was added. The resulting mixture was stirred at room temperature for 10 minutes, and 100 μL each of 1N-HCl (produced by Sigma Aldrich Japan) was added while observing the degree of coloring. The sample solution was transferred to a 96-well ELISA plate, and the absorbance at 450 nm was measured with a plate reader (type MPR-A4i II, produced by Tosoh Corporation). A higher absorbance indicates a larger amount of adsorbed fibrinogen. The relative adsorption ratio of fibrinogen means the relative percentage (%) of the absorbance of the sample taking the absorbance of a film as 100, which film is a poly(methyl methacrylate) film immersed in deaerated pure water and irradiated with D-ray at a dose of 25 kGy.

Example 1

In accordance with the procedures described in 2.(1), modification and sterilization of poly(methyl methacrylate) hollow fiber membranes in a module were simultaneously carried out using an aqueous solution containing 0.1% by weight of ethanol (hereinafter referred to as "aqueous 0.1% by weight ethanol solution"). Thereafter, the ethanol solution was replaced with pure water and the module was again irradiated with γ-ray as described in 3.(1). The dose of the γ-ray was 28 kGy. The samples before and after replacement with pure water and irradiation with γ-ray were subjected to the human platelet adhesion test and to the fibrinogen adsorption test as described in 3.(1) and 3.(2), respectively.

The results are shown in Table 1. That is, the modified base material had a high blood compatibility and had an excellent radical resistance, which retained the good blood compatibility even after the second irradiation with γ-ray.

Example 2

The same operations as in Example 1 were repeated except that aqueous 0.01% by weight ethanol solution was used for the module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, the modified base material had a high blood compatibility and had an excellent radical resistance, which retained the good blood compatibility even after the second irradiation with γ-ray.

Example 3

The same operations as in Example 1 were repeated except that aqueous 0.1% by weight n-hexanol solution was used for the module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, the modified base material had a high blood compatibility and had an excellent radical resistance, which retained the good blood compatibility even after the second irradiation with γ-ray.

Example 4

The same operations as in Example 1 were repeated except that aqueous 0.1% by weight 1,3-propanediol solution was used for the module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, the modified base material had a high blood compatibility and had an excellent radical resistance, which retained the good blood compatibility even after the second irradiation with γ-ray.

Example 5

A modified film was prepared by using aqueous 0.1% by weight ethanol solution for a poly(methyl methacrylate) film in accordance with the procedures described in 2.(2). The replacement with pure water and the second irradiation with γ-ray were carried out as described above. The samples before and after the replacement with pure water and irradiation with γ-ray were subjected to the human platelet adhesion test and to the fibrinogen adsorption test.

The results are shown in Table 1. That is, the modified base material had a high blood compatibility and had an excellent radical resistance, which retained the good blood compatibility even after the second irradiation with γ-ray.

Example 6

The same operations as in Example 5 were repeated except that aqueous 0.1% by weight 1,3-propanediol solution was used for a poly(methyl methacrylate) film, and the film was subjected to the human platelet adhesion test and to the fibrinogen adsorption test. The dose of the γ-ray used for irradiating the film again after the replacement with water was 28 kGy.

The results are shown in Table 1. That is, the modified base material had a high blood compatibility and had an excellent radical resistance, which retained the good blood compatibility even after the second irradiation with γ-ray.

Example 7

A modified film was prepared by using aqueous 0.1% by weight ethanol solution for a polylactic acid film in accordance with the procedures described in 2.(2). The replacement with pure water and the second irradiation with γ-ray were carried out as described above. The samples before and after the replacement with pure water and irradiation with γ-ray were subjected to the human platelet adhesion test and to the fibrinogen adsorption test.

The results are shown in Table 1. That is, the modified base material had a high blood compatibility and had an excellent radical resistance, which retained the good blood compatibility even after the second irradiation with γ-ray.

Example 8

The same operations as in Example 7 were repeated except that aqueous 0.1% by weight 1,3-propanediol solution was used for a polylactic acid film, and the film was subjected to the human platelet adhesion test and to the fibrinogen adsorption test. The dose of the γ-ray used for irradiating the film again after the replacement with water was 28 kGy.

The results are shown in Table 1. That is, the modified base material had a high blood compatibility and had an excellent radical resistance, which retained the good blood compatibility even after the second irradiation with γ-ray.

Example 9

A module of poly(methyl methacrylate) hollow fiber membranes was subjected to the platelet adhesion test without irradiation of γ-ray. The number of adhered platelets was 0.23 (platelets/$4.3 \times 10^3$ $\mu m^2$), so that the film exhibited good blood compatibility. Such a module containing hollow fiber membranes was filled with aqueous 0.046% by weight (0.01 mol/L) ethanol solution (produced by Aldrich) by introducing the ethanol solution from the blood inlet 3, guiding the solution to the dialysate outlet 9 through the blood outlet 4, and flowing the solution to the dialysate inlet 8. The module was then irradiated with γ-ray at a dose of 27 kGy. The hollow fibers in the module were cut out and subjected to the platelet adhesion test. Using as the positive control "Filtryzer" BG-1.6U (product lot: 91110412), an artificial kidney produced by TORAY, and using as the negative control artificial kidney PS-1.6UW (product lot: 1Y7335) produced by Kawasumi Laboratories, the validity of the platelet adhesion test was confirmed. In the Examples and Comparative Examples below, similar samples were used and the validity of the platelet adhesion test was confirmed. The results are shown in Table 2.

Example 10

The same operations as in Example 9 were repeated except that aqueous 0.060% by weight (0.01 mol/L) 2-propanol (produced by Aldrich) was used, and the film was subjected to the platelet adhesion test. The dose of the γ-ray was 27 kGy. The results are shown in Table 2.

Comparative Example 1

A module of poly(methyl methacrylate) hollow fiber membranes were sterilized in the same manner as in 2.(1) described above except that pure water was used in place of the aqueous solution of alcohol or polymer used for the modification by the procedures described in 2.(1). Thereafter, the replacement with pure water was carried out by the method described above, and the module was again irradiated with γ-ray. The samples before and after the replacement with pure water and irradiation with γ-ray were subjected to the platelet adhesion test and to the fibrinogen adsorption test.

The results are shown in Table 1. That is, the base material had a poor blood compatibility.

Comparative Example 2

The same operations as in Comparative Example 1 were repeated except that aqueous 0.1% by weight ethylene glycol solution was used for a module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, the base material had a poor blood compatibility.

Comparative Example 3

The same operations as in Comparative Example 1 were repeated except that aqueous 0.1% by weight propylene glycol solution was used for a module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, although the base material had a high blood compatibility, the modified base material had a poor radical resistance as it could not retain the good blood compatibility after the second irradiation of γ-ray.

Comparative Example 4

The same operations as in Comparative Example 1 were repeated except that aqueous 0.1% by weight glycerin solution was used for a module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, the base material had a poor blood compatibility.

Comparative Example 5

The same operations as in Comparative Example 1 were repeated except that aqueous 0.1% by weight polyvinyl alcohol (produced by Aldrich, weight average molecular weight: 10,000, hydrophilic units: 80%) solution was used for a module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, although the base material had a high blood compatibility, the modified base material had a poor radical resistance as it could not retain the good blood compatibility after the second irradiation of γ-ray.

Comparative Example 6

The same operations as in Comparative Example 1 were repeated except that aqueous 0.1% by weight polyvinylpyrrolidone (produced by BASF, weight average molecular weight: 10,000) solution was used for a module of poly(methyl methacrylate) hollow fiber membranes, and the membranes were subjected to the human platelet adhesion test and to the fibrinogen adsorption test. The dose of the γ-ray used for irradiating the membranes again after the replacement with water was 28 kGy.

The results are shown in Table 1. That is, although the base material had a high blood compatibility, the modified base material had a poor radical resistance as it could not retain the good blood compatibility after the second irradiation of γ-ray.

Comparative Example 7

A poly(methyl methacrylate) film was sterilized in the same manner as in 2.(1) described above except that pure water was used in place of the aqueous solution of alcohol or polymer used for the modification by the procedures described in 2.(1). Thereafter, the replacement with pure water was carried out by the method described above, and the film was again irradiated with γ-ray. The samples before and after the replacement with pure water and irradiation with γ-ray were subjected to the platelet adhesion test and to the fibrinogen adsorption test.

The results are shown in Table 1. That is, the base material had a poor blood compatibility.

Comparative Example 8

The same operations as in Comparative Example 7 were repeated except that aqueous 0.1% by weight glycerin solution was used for a poly(methyl methacrylate) film, and the film was subjected to the human platelet adhesion test and to the fibrinogen adsorption test. The dose of the γ-ray used for irradiating the film again after the replacement with water was 28 kGy.

The results are shown in Table 1. That is, the base material had a poor blood compatibility.

Comparative Example 9

A polylactic acid film was sterilized in the same manner as in 2.(1) described above except that pure water was used in place of the aqueous solution of alcohol or polymer used for the modification by the procedures described in 2.(1). Thereafter, the replacement with pure water was carried out by the method described above, and the film was again irradiated with γ-ray. The samples before and after the replacement with pure water and irradiation with γ-ray were subjected to the platelet adhesion test and to the fibrinogen adsorption test.

The results are shown in Table 1. That is, the base material had a poor blood compatibility.

Comparative Example 10

The same operations as in Comparative Example 9 were repeated except that aqueous 0.1% by weight glycerin solution was used for a polylactic acid film, and the film was subjected to the human platelet adhesion test and to the fibrinogen adsorption test. The dose of the P-ray used for irradiating the film again after the replacement with water was 28 kGy.

The results are shown in Table 1. That is, the base material had a poor blood compatibility.

Comparative Example 11

A module of poly(methyl methacrylate) hollow fiber membranes was filled with pure water by flowing the pure water from the blood inlet 3 to the blood outlet 4, and then from the dialysate outlet 9 to the dialysate inlet 8. Thereafter, the module was irradiated with γ-ray. The dose of the γ-ray was 27 kGy. The hollow fiber membranes in the module were cut out and subjected to the platelet adhesion test. The results are shown in Table 1. The number of adhered platelets was very large, so that it was seen that blood compatibility was deteriorated by the modification by the γ-ray.

Comparative Example 12

The same operations as in Example 11 were repeated except that aqueous 0.19% by weight (0.01 mol/L) sodium pyrosulfite (produced by Aldrich) was used, and the film was subjected to the platelet adhesion test. The dose of the γ-ray was 27 kGy. The results are shown in Table 2.

TABLE 1

| | Substrate | Modifier and Concentration of Aqueous Solution | Form | Number of Adhered Platelets[1] (count/4.3 × 10³ μm²) | | Relative Adsorption Ratio of Fibrinogen[2] (%) | |
|---|---|---|---|---|---|---|---|
| | | | | Before Irradiation of γ-ray in Water | After Irradiation of γ-ray in Water | Before Irradiation of γ-ray in Water | After Irradiation of γ-ray in Water |
| Example 1 | poly(methyl methacrylate) | ethanol 0.1 wt % | hollow fiber membrane | 0.9 | 6.4 | 43 | 61 |
| Example 2 | poly(methyl methacrylate) | ethanol 0.01 wt % | hollow fiber membrane | 2.3 | 5.3 | 51 | 64 |
| Example 3 | poly(methyl methacrylate) | n-hexanol 0.1 wt % | hollow fiber membrane | 0.7 | 9.7 | 48 | 58 |
| Example 4 | poly(methyl methacrylate) | 1,3-propanediol 0.1 wt % | hollow fiber membrane | 3.7 | 12.3 | 64 | 69 |
| Example 5 | poly(methyl methacrylate) | ethanol 0.1 wt % | film | 1.1 | 4.8 | 44 | 53 |
| Example 6 | poly(methyl methacrylate) | 1,3-propanediol 0.1 wt % | film | 4.3 | 11.9 | 58 | 71 |
| Example 7 | polylactic acid | ethanol 0.1 wt % | film | 1.1 | 6.2 | 55 | 60 |
| Example 8 | polylactic acid | 1,3-propanediol 0.1 wt % | film | 2.3 | 9.8 | 67 | 74 |
| Comparative Example 1 | poly(methyl methacrylate) | pure water | hollow fiber membrane | >100 | >100 | 101 | >130 |
| Comparative Example 2 | poly(methyl methacrylate) | ethylene glycol 0.1 wt % | hollow fiber membrane | 22.5 | >100 | 97 | >130 |
| Comparative Example 3 | poly(methyl methacrylate) | propylene glycol 0.1 wt % | hollow fiber membrane | 6.24 | >100 | 80 | >130 |
| Comparative | poly(methyl | glycerine 0.1 wt % | hollow fiber | >100 | >100 | >130 | >130 |

TABLE 1-continued

| | Substrate | Modifier and Concentration of Aqueous Solution | Form | Number of Adhered Platelets[1] (count/4.3 × 10³ μm²) Before Irradiation of γ-ray in Water | After Irradiation of γ-ray in Water | Relative Adsorption Ratio of Fibrinogen[2] (%) Before Irradiation of γ-ray in Water | After Irradiation of γ-ray in Water |
|---|---|---|---|---|---|---|---|
| Example 4 | methacrylate) | | membrane | | | | |
| Comparative Example 5 | poly(methyl methacrylate) | polyvinyl alcohol 0.1 wt % | hollow fiber membrane | 0.9 | >100 | 105 | >130 |
| Comparative Example 6 | poly(methyl methacrylate) | polyvinylpyrrolidone 0.1 wt % + ethanol 0.1 wt % | hollow fiber membrane | 1.2 | >100 | 80 | >130 |
| Comparative Example 7 | poly(methyl methacrylate) | pure water | film | >100 | >100 | 100 | >130 |
| Comparative Example 8 | poly(methyl methacrylate) | glycerine 0.1 wt % | film | >100 | >100 | >130 | >130 |
| Comparative Example 9 | polylactic acid | pure water | film | >100 | >100 | >130 | >130 |
| Comparative Example 10 | polylactic acid | glycerine 0.1 wt % | film | >100 | >100 | >130 | >130 |

[1]In "Number of Adhered Platelets" column, ">100" means "over 100".
[2]In "Relative Adsorption Ratio of Fibrinogen" column, ">130" means that absorbance of the sample is over the upper limit of the range of measurement.

TABLE 2

Results of Platelet Adhesion Test

| | | Number of Adhered Platelets |
|---|---|---|
| Example 9 | ethanol (0.01 mol/L) | 0.27 |
| Example 10 | 2-propanol (0.01 mol/L) | 0.32 |
| Comparative Example 11 | none (water) | 40.8 |
| Comparative Example 12 | sodium pyrosulfite (0.01 mol/L) | 15.8 |

The invention claimed is:

1. A process for producing a modified base material, characterized by irradiating a base material comprising an ester group-containing polymer with radiation while said base material is contacted with an aqueous solution of a monohydric alcohol having a concentration of from 0.0001% by weight to 0.1% by weight, wherein said aqueous solution of alcohol and/or said base material do(es) not substantially contain a water-soluble polymer.

2. The process for producing a modified base material, according to claim 1, characterized in that said ester group-containing polymer is a methacrylic polymer.

3. The process for producing a modified base material, according to claim 2, characterized in that said methacrylic polymer is poly(methyl methacrylate) or a derivative thereof.

* * * * *